United States Patent [19]

Morrison

[11] Patent Number: 5,752,933
[45] Date of Patent: May 19, 1998

[54] PROSTAGLANDIN APPLICATOR

[76] Inventor: Malcolm S. F. G. Morrison, 42 Cambrai Avenue, Engadine, New South Wales, Australia, 2233

[21] Appl. No.: 780,403

[22] Filed: Jan. 9, 1997

[30] Foreign Application Priority Data

Jan. 29, 1996 [AU] Australia .................. P00069

[51] Int. Cl.⁶ .................. A61M 5/00; A61F 5/00
[52] U.S. Cl. .................. 604/116; 600/38; 128/883; 128/845
[58] Field of Search .................. 604/116, 117, 604/180, 46; 128/845, 843, DIG. 26; 600/38–41

[56] References Cited

U.S. PATENT DOCUMENTS 5,192,271 3/1993 Kalb et al. .................. 604/116
5,238,009 8/1993 House .................. 128/883
5,628,329 5/1997 Bennett et al. .................. 128/842

*Primary Examiner*—Sam Rimell
*Assistant Examiner*—Robert V. Racunas
*Attorney, Agent, or Firm*—Jacobson & Johnson

[57] ABSTRACT

There is an applicator for assisting the injection of a drug such as prostaglandin into a penis. The applicator may comprise an elongated guide member having disposed at one end thereof a support means and syringe ports on said support means. The relative orientation of the guide member, support means and syringe ports being such that in use of the applicator when the guide member is aligned along the length of the penis and the support means is at or adjacent the base thereof said syringe ports are positioned whereby the needle of a syringe when inserted through one of said syringe ports enters the penis tissue at a predetermined angle and/or to a predetermined depth.

9 Claims, 7 Drawing Sheets

5,752,933

PROSTAGLANDIN APPLICATOR

FIELD OF THE INVENTION

This invention relates to apparatus for assisting the administration of a drug. More particularly although not exclusively it provides an applicator to facilitate the injection of prostaglandin into the penis as a therapy for male impotence.

BACKGROUND OF THE INVENTION

For certain types of male impotence one form of therapy is the syringe injection of Prostaglandin directly into the Glans Penis and Corpus Spongiosum muscles. This has the effect of producing a strong temporary erection so that sexual intercourse can take place. The injection site is at the base of the penis and the angle and depth of needle insertion are of critical importance to the success of the procedure. Incorrect insertion as well as reducing the effectiveness of the prostaglandin can also damage nerves and/or blood vessels within the penis. For privacy reasons most men wish to inject themselves while alone and thus the correct insertion of the needle is difficult especially for persons whose view of their penis is obstructed due to obesity for example. Also it may be necessary for an individual who through deformity or trauma has not the dexterity to administer to himself and requires assistance from his partner. The partner however may be totally unsure of how to be effective.

SUMMARY OF THE INVENTION

It is therefore an object of this invention to ameliorate the aforementioned problem and accordingly there is disclosed an applicator for assisting the injection of prostaglandin into a penis, said applicator comprising an elongated guide member having disposed at one end support means and at least one syringe port on said support means, the relative orientation of said guide member, support means and syringe port being such that in use of the applicator when said guide member is aligned along the length of the penis and the support means is at or adjacent the base thereof said at least one syringe port is positioned whereby the needle of a syringe when inserted through said port enters the penis tissue at a predetermined angle and/or to a predetermined depth.

BRIEF DESCRIPTION OF THE DRAWINGS

The currently preferred form of this invention will now be described with reference to the attached drawings in which.

DETAILED DESCRIPTION

Figure 1:
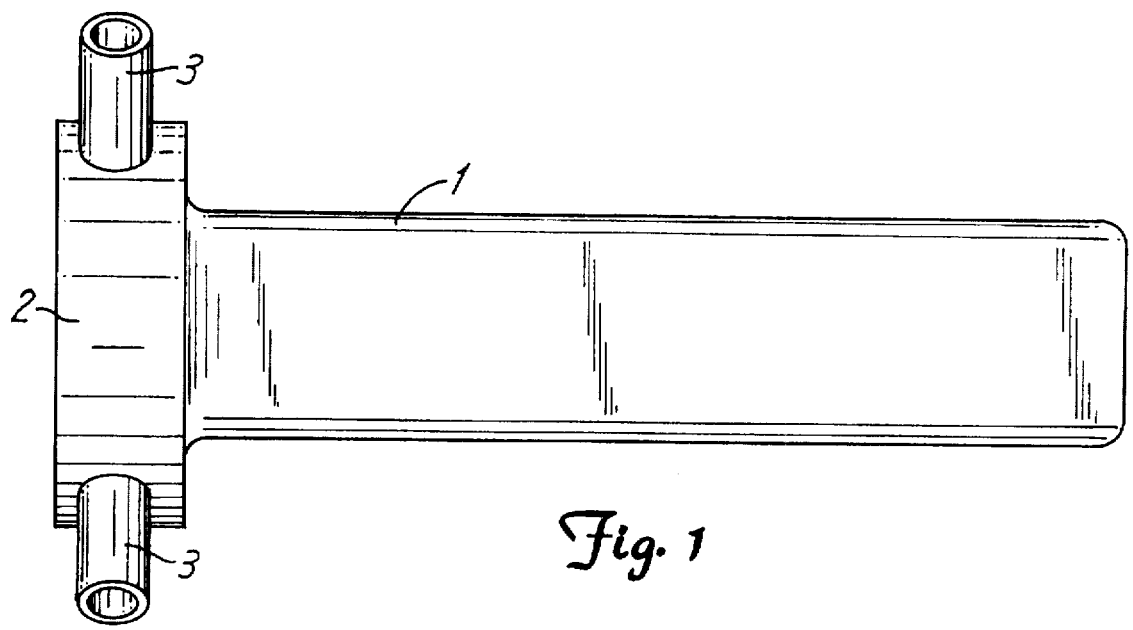
FIG. 1 is a schematic plan view of one form of applicator according to this concept.
Figure 2:
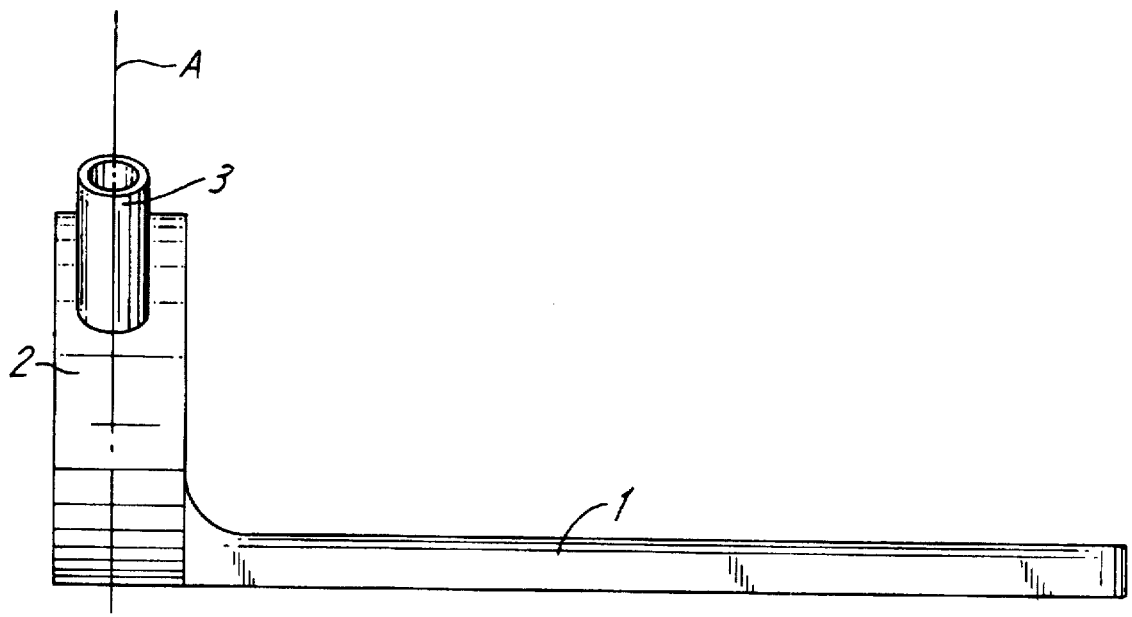
FIG. 2 is a side view of the applicator of FIG. 1.
Figure 3:
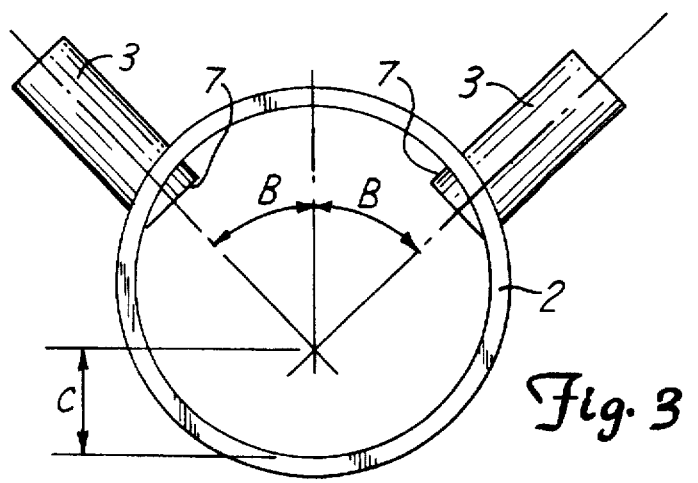
FIG. 3 is an end view of the applicator.

Referring first to FIGS. 1 to 3 the applicator may be constructed from moulded plastic and may comprise an elongated guide member 1 of width 30 mm and length 150 mm. At one end of this guide there is formed a ring shaped support member 2 which is of sufficient internal diameter to encircle the human penis. With this embodiment the internal diameter is about 51 mm however other diameters may also be found suitable depending upon the size and type of syringe used. There are two cylindrical syringe ports 3 mounted through this support member. As best shown in FIGS. 2 and 3 these ports are located in a plane A at 90 degrees to the length of the guide member 1 and are also fixed symmetrically at angles B of 45 degrees to each side of the vertical. In this position the centre lines of the ports intersect at a distance C of about 12 mm above the base of the ring as shown. Preferably these ports are about 28 mm in length, 10 mm ID and 11 mm OD. Preferably the applicator also includes a positioning tube 3A which is adapted for a close tolerance sliding fit both over the barrel of the syringe and within the ports 3.

Figure 6:
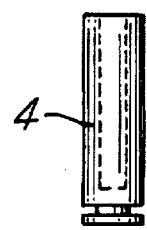
FIG. 6 is a side view of a cap for placing over the syringe needle prior to insertion into the positioning tube.
Figure 4:
FIG. 4 shows side and end views of a positioning tube for the syringe.
Figure 5:
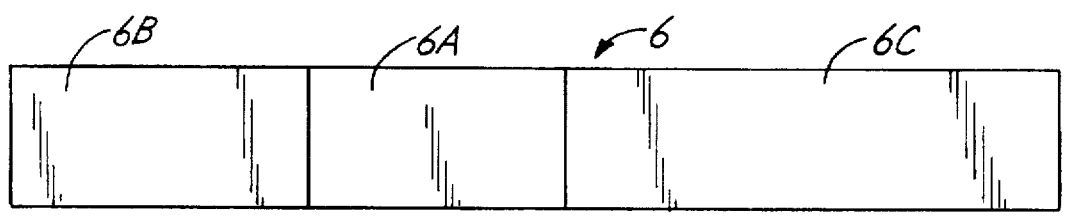
FIG. 5 shows side and top views of a strap for holding the applicator in place during use.
Figure 5:
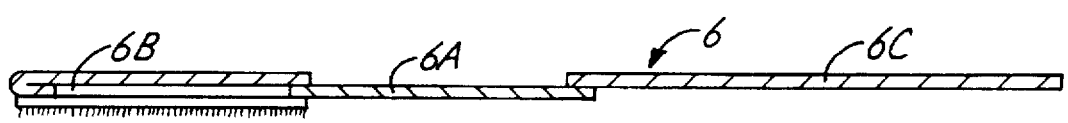
Figure 7:
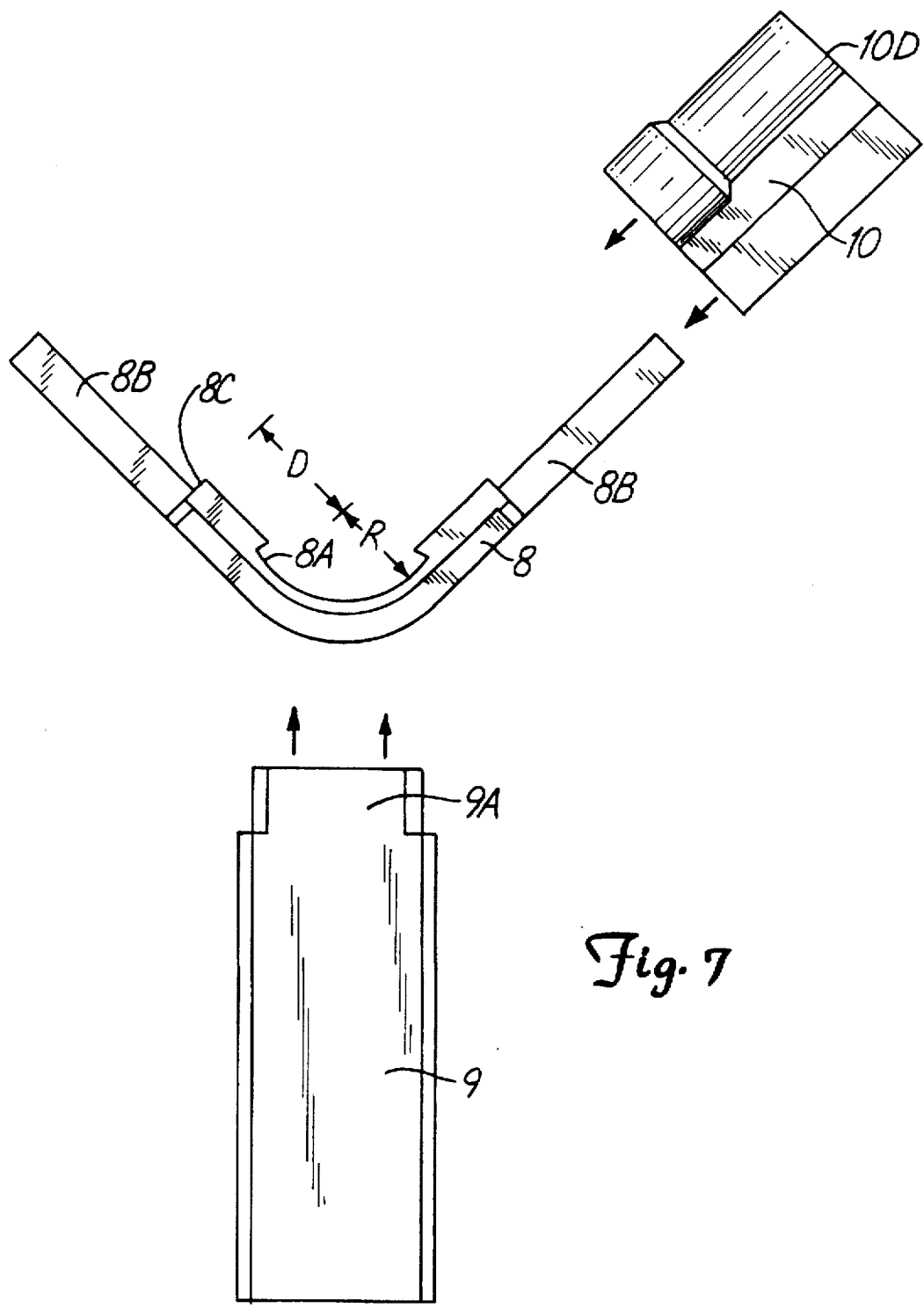
FIG. 7 shows an exploded view of a second form of applicator according to this invention.

In use a fresh syringe is first unpacked, filled with prostaglandin in accordance with conventional hygienic procedures and the needle again covered with a specially shaped Re-Cap unit 4 (see FIG. 6) which preserves sterility while still allowing insertion of the syringe barrel in through one end of the positioning tube 3A. Once the Re-Cap 4 protrudes out from the other end of the tube the Re-Cap is removed to expose the needle and the syringe is drawn back sufficiently to bring the needle fully within tube 3A. The penis is then inserted through the support ring 2 of the applicator and fully extended along the top of the guide member 1 so that said support member 2 is located at the base of the penis. When the applicator is positioned correctly the two syringe ports 3 should be located symmetrically on each side of the penis at about 45 degrees to the vertical as best shown in FIG. 3 when the user is standing upright. The strap 6 is then wrapped around the penis and guide member 1 to hold the penis in its extended position. Preferably this strap as best shown in FIG. 5 comprises a central elastic section 6A of length 40 mm together with velcro and binding tape sections 6B and 6C of 40 mm and 70 mm respectively at opposite ends. The strap is preferably placed so that the velcro section is located under the guide member and the elastic portion extends up around the penis. The tape section then loops back under the guide member and attaches to the velcro. The previously prepared positioning tube and loaded syringe is then inserted into one of the two syringe ports 3 without disturbing the relative positions of the needle within the positioning tube or the plunger of the syringe. After swabbing clean the area of the penis below the selected port the syringe barrel is pushed down the positioning tube as far as it will go and the plunger depressed to inject the prostaglandin into the penis tissue. Preferably the lower ends 7 of the ports have internal ridges to limit the insertion of the positioning tube. The entire unit consisting of the positioning tube and empty syringe is now removed by carefully withdrawing them from the port. Finally the applicator is unstrapped and removed from the penis.

A second embodiment of the invention is shown in FIGS. 7 to 13. This form of applicator is adapted for use with the CAVERJECT COMPANION PACK as marketed in Australia by Upjohn Pty. Limited of Rydalmere NSW. The pack contains a specially designed Deltaject needle, 2.5 ml. syringe and alcohol swab for self-injection of prostaglandin.

Referring first to FIGS. 7 to 11 the applicator consists of four basic components ie. a body portion comprising a pair of outwardly extending arms 8, a trough shaped guide member 9, a positioning sleeve 10 and an elastic strap 11 with velcro fastening pad 11A. The body portion 8 slidably connects onto the end of the guide member 9 so that the arms when in a position of use extend out at an angle of about 45 degrees to the vertical and are situated in a plane substantially perpendicular to the length of the guide member. Although the invention is not restricted to any particular mechanism for connecting the body portion and guide member in this case one end of the guide member is formed into a tongue 9A which is a push fit into a rounded correspondingly shaped groove 8A at the base of the two arms. Preferably the radius "R" of this groove is about 14 mm as shown. The invention however is not limited to this dimension. The upper segments 8B of the arms are preferably rectangular in cross-section down to shoulder stops 8C which are preferably located a distance D of about 20 mm up from the centre of radius of the groove 8A. Again however the invention is not limited to this particular dimension. The arm segments 8B are designed for a close tolerance sliding fit into a correspondingly shaped aperture 10A in the positioning sleeve (see FIG. 10) so that the sleeve slides down onto the shoulders 8C of the arms. The positioning sleeve also includes a socket 10B which is aligned parallel to the aperture 10A and is adapted to receive the barrel of the CAVERJECT syringe and an end flange of the DELTAJECT needle by means of the enlarged end section 10C. The length of the positioning sleeve 10 and the positions of the shoulder stops 8C are preferably chosen so as to enable the correct depth of needle penetration with the CAVERJECT syringe as described later. With this particular embodiment the sleeve is preferably about 35 mm. in length however the invention is not limited to this dimension.

Figure 12:
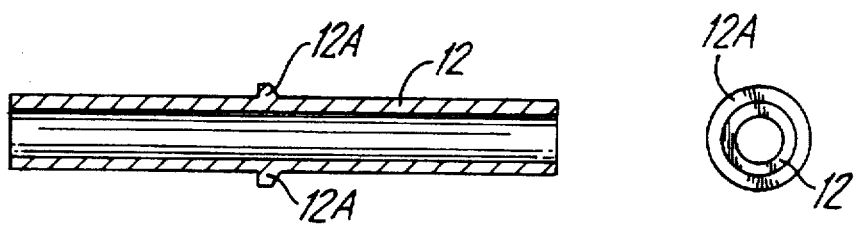
FIG. 12 shows cross-sectional side and end views of the adapter to enable the alternative use of a conventional 1 ml. syringe.
Figure 13:
FIG. 13 shows cross-sectional side and end views of a needle protector cap for use with the adapter of FIG. 12.

To enable the alternative use of a conventional 1 ml syringe an adaptor tube 12 and protector cap 13 as shown in FIGS. 12 and 13 may be used. The adaptor tube is dimensioned to be a sliding fit into the aperture 10B of the positioning sleeve. In use it receives the barrel of the syringe and then may be inserted into the positioning sleeve until a flange 12A about midway along its length abuts the end 10D of the sleeve. The length of the adapter tube 12 (in this case about 75 mm) as well as the position of the flange 12A are chosen so as to ensure the correct depth of penetration when fitted into the positioning sleeve as described later.

In use of this applicator with the CAVERJECT syringe the following steps should preferably be followed:

1. Attach the guide member to the body portion and place the elastic holding stap over the guide member
2. Remove the CAVERJECT syringe from the companion pack
3. Insert the syringe barrel into the positioning sleeve from the narrower end 10D and push it through as far as possible.
4. Twist the plastic end cap off the CAVERJECT syringe barrel and replace it with the DELTAJECT needle from the companion pack.
5. Remove the protective cover from the DELTAJECT needle.
6. Fill the syringe with the prescribed dose of prostaglandin in accordance with conventional hygenic procedures.
7. Draw the loaded syringe with the needle unsheathed back into the positioning sleeve.
8. Fit the positioning sleeve with the prepared syringe in place onto one of the arms of the body portion. Preferably the positions of use are rotated between the two arms.
9. Place the user's penis in position along the guide member of the assembled applicator with the arms about 45 degrees to the centre-line of the body and closest to the pubic area. Fit the elastic holding strap around the penis so as to hold it firmly along the length of the guide member.
10. Swab that area of the penis directly in line with the positioning sleeve.
11. Push the barrel of the syringe firmly down to cause the DELTAJECT needle to pierce the penile tissue. The design of the DELTAJECT needle prevents the the needle penetrating too deeply into the penis.
12. After the needle is fully inserted depress the syringe plunger to inject the prostaglandin into the penile tissue.
13. When the dose of prostaglandin has been injected remove the entire positioning sleeve with the syringe and needle still in place from the arm of the body portion.
14. Release the holding strap from around the penis and disassemble the applicator. Re-cap and safely dispose of the syringe and needle.

In order to use a conventional 1 ml syringe an adaptor tube and needle protector cap as shown in FIGS. 12 and 13 may be used with the applicator.

The preferred method of use in this case is as follows:
1. A fresh 1 ml syringe is obtained and the standard needle cap is replaced with the needle protector cap of FIG. 11.
2. The syringe is inserted into the adapter tube as far possible.
3. The protector cap is removed from the needle and the syringe is filled with prostaglandin in accordance conventional hygenic procedures.
4. The cap is replaced over the needle and the syringe withdrawn back up into the adapter tube to leave only about 2 mm of the protector cap exposed.
5. The adapter tube with the loaded syringe inside is inserted into the positioning sleeve from the aperture end 10D and positioned so that only the exposed 2 mm of the protector cap extends out the opposite end of the positioning sleeve.
6. The protector cap is again removed, the positioning sleeve located on one of the arms and the penis strapped onto the guide member and swabbed as described earlier in relation to the CAVERJECT syringe.
7. The adapter tube is pushed down into the positioning sleeve until the flange 12A abuts the end 10D.
8. After the adapter tube has been so positioned the barrel of the syringe is pushed firmly downward as far as it will go causing the needle to pierce the penis. The syringe plunger is then depressed to inject the prescribed dose of prostaglandin.
9. The procedure is completed in a similar manner to steps 13 and 14 with the CAVERJECT syringe.

A further example of this invention is shown in FIGS. 14, 15, 16 and 17. In this case the trough shaped guide member 14 is formed as one piece with a body portion comprising a set of outwardly extending arms 15. As with previous examples when the applicator is in a position of use as shown the arms extend out at an angle of about 45 degrees to the vertical and are situated in a plane substantially perpendicular to the length of the guide member 14. Each of the arms 15 ends at a holding port 16. The axial centre lines of these ports preferably intersect at a point E about 12 mm above the trough of the guide member 14. The adaptor 17 for holding the syringe is with this example formed of two mating halves 17A and 17B (see FIG. 16). As example of one of these halves is shown in cross-section in FIG. 17. It includes a spring finger 18 which protrudes out from the inside wall 19 of the adaptor 19 by a distance with this example of about 0.5 mm. In use of the device the two halves are positioned around the outside of the syringe barrel with the smaller diameter end 20 toward the plunger end. The enlarged plug shaped end 21 of the adaptor facing the needle is then inserted into one of the holding ports 16 up to the shoulder 22 (see FIG. 14). Preferably the relative diameters of the end 21 and holding port 16 are chosen so that the two components are a push fit. With the end 21 inserted into the holding port 16 the two halves 17A and 17B are held together and the spring fingers 18 grip the syringe barrel. The syringe barrel is then drawn back up the adaptor 17 until the end of the needle protector cap (described earlier with reference to FIG. 13) protrudes slightly below the bottom edge 23 of the holding port. Finally, the user's penis is located along the guide member 14 using the Velcro strap 24 and prepared as described earlier, the protector cap is removed, the syringe pushed down to the correct needle penetration depth as determined by the adaptor position and the prostaglandin injected as with previous examples.

It will thus be appreciated that this invention at least in the form of the embodiment described provides a novel and unique form of applicator for the administration of prostaglandin. Clearly however the examples disclosed are only the currently preferred forms of the invention and a wide variety of modifications may be made which would be apparent to a person skilled in the art. For example the shape, configuration and size of the applicatosr may be changed according to design preference. Also while the applicators are preferably constructed from moulded plastic the invention extends to the use of any other suitable material.

Figure 8:
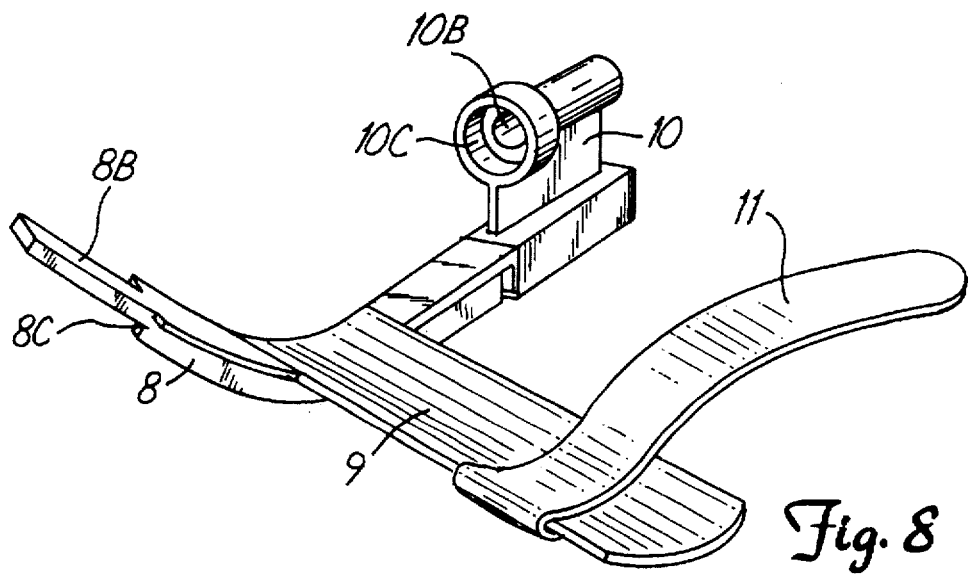
FIG. 8 is a perspective view of the assembled applicator of FIG. 7.
Figure 9:
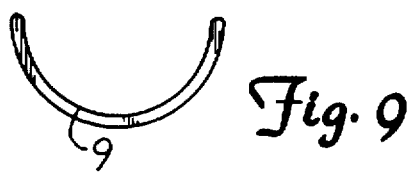
FIG. 9 is an end view of the guide member of FIG. 7.
Figure 10:
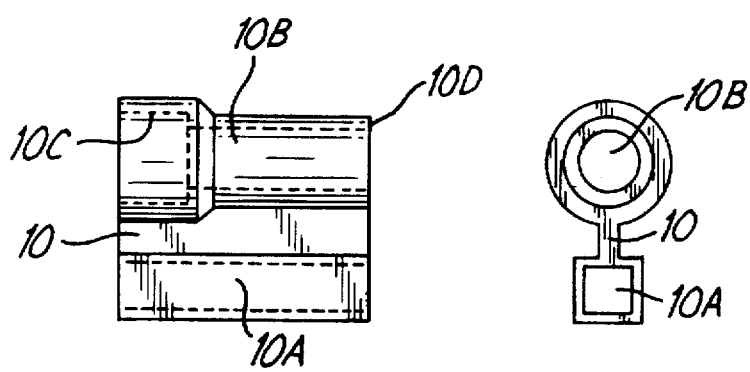
FIG. 10 shows side and end views of the positioning sleeve.
Figure 11:
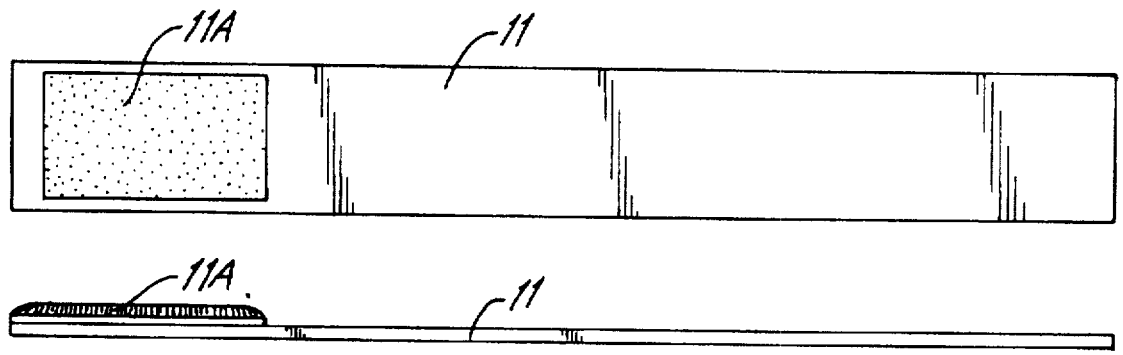
FIG. 11 shows plan and side views of the elastic strap for use with the applicator of FIG. 7.
Figure 14:
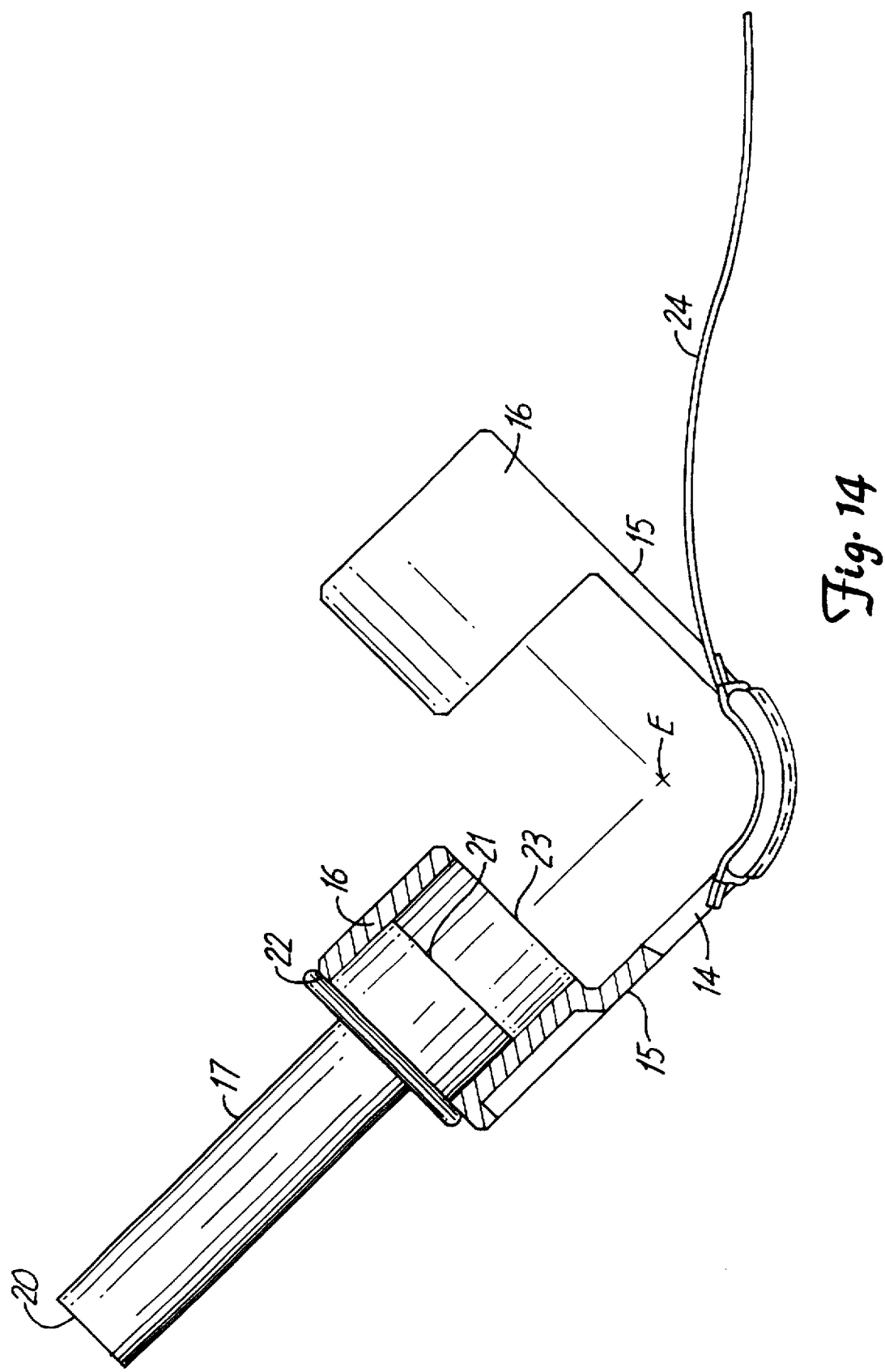
FIG. 14 is an end view in partial cross-section of a third form of applicator according to this invention.
Figure 15:
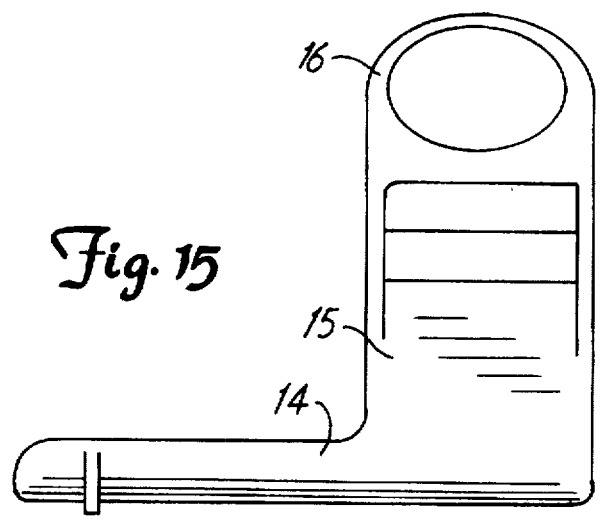
FIG. 15 is a side view of the applicator of FIG. 14.
Figure 16:
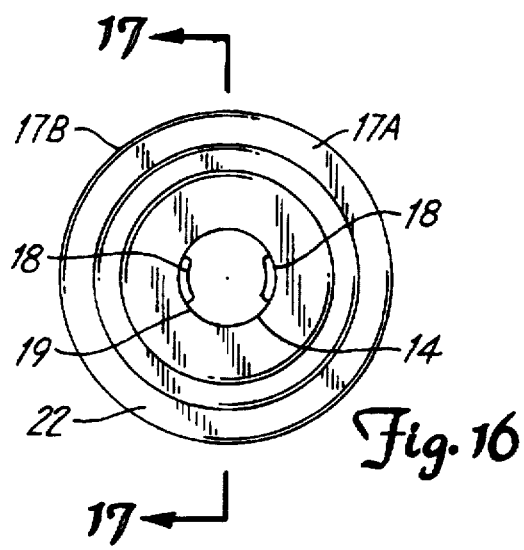
FIG. 16 is an end view of the preferred form of adaptor for the applicator of FIG. 14.
Figure 17:
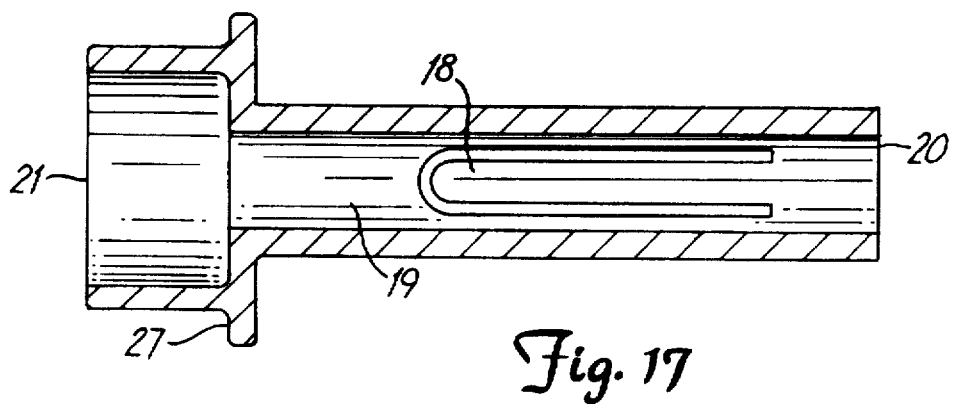
FIG. 17 is a side view of part of the adaptor of FIG. 16.

For the purposes of this specification expressions such as "vertical", "side" and "down" etc. refer to the applicators in a position of use as illustrated for example in FIGS. 2, 8 & 14 and are not to be read as necessarily limiting.

The claims defining the invention are as follows:

1. An applicator for assisting the injection of an erection causing drug into a penis, said applicator comprising an elongated guide member shaped to be locatable along the length of the penis and having disposed at one end a support means and at least one syringe alignment means on said support means, the relative orientation of said guide member, a support means and syringe alignment means being such that in use of the applicator when the guide member is located along the length of the penis and the support means is at or adjacent the pubic area said at least one syringe alignment means is positioned whereby a needle of a syringe when inserted through said syringe alignment means enters the penis tissue at a predetermined angle or to a predetermined depth.

2. The applicator as claimed in claim 1 wherein said penis tissue is the Glans Penis or Corpus Spongiosum Muscle.

3. The applicator as claimed in claim 2 wherein said predetermined angle is about 45 degrees to the vertical.

4. The applicator as claimed in claim 3 wherein said at least one syringe alignment means is located in a plane at about 90 degrees to the length of the guide member.

5. The applicator as claimed in claim 4 wherein there is provision for mounting said syringe alignment means on either side of the guide member.

6. The applicator as claimed in claim 4 and further including a tube which is adapted for a close tolerance sliding fit both over a barrel of said syringe and within said syringe alignment means.

7. The applicator as claimed in claim 5 wherein said provision for mounting said syringe alignment means comprises a pair of arms extending out to each side of said guide member, the outer end portions of said arms being adapted to slidably engage said syringe alignment means.

8. A method of injecting an erection causing drug into a penis using the applicator as claimed in any one of claims 1 to 6, said method including the steps of:
    preparing a syringe with a dose of said drug,
    fitting said applicator on said penis whereby said penis is aligned along the length of said guide member, the support means being at or adjacent the pubic area and said at least one syringe alignment means being located about 45 degrees to one side of the vertical,
    inserting said syringe through said syringe alignment means whereby the needle penetrates the penis tissue, and
    injecting said drug into the penis tissue.

9. The method as claimed in claim 9 wherein said syringe is inserted into a tube before being inserted into said syringe alignment means.

\* \* \* \* \*